Mar. 13, 1934. M. KRAUSE Plant Pat. 87
ROSE
Filed Nov. 20, 1933
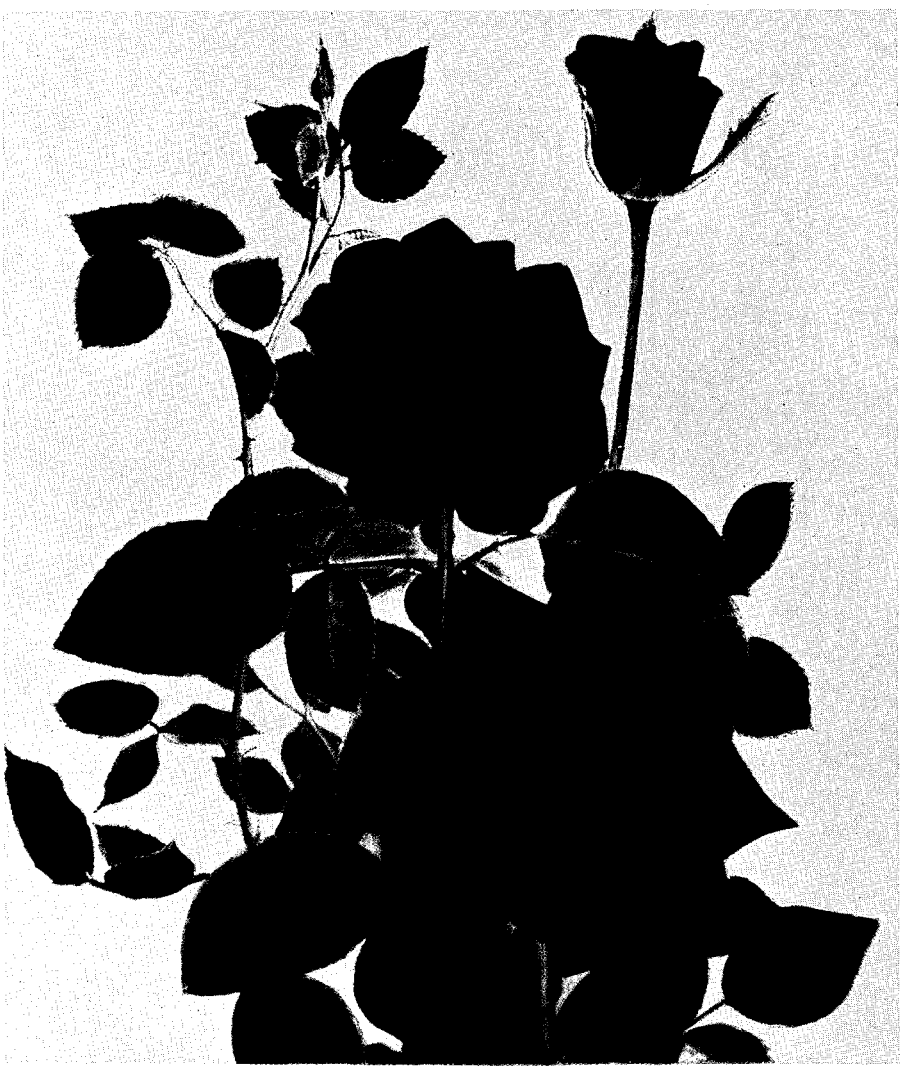
Inventor
Max Krause
By Robb & Robb
M. P. Macdonald
Attorneys Patented Mar. 13, 1934

Plant Pat. 87

UNITED STATES PATENT OFFICE

87

ROSE

Max Krause, Hasloh in Holstein, Germany assignor to The Conard-Pyle Company, West Grove, Pa.

Application November 20, 1933, Serial No. 698,909

1 Claim. (Cl. 47—61)

This invention relates to a new and distinct variety of rose, the successful result of definite breeding efforts having as their main objective the production of a darker rose than any now in commerce.

This new rose was produced by crossing the hybrid tea roses Chateau de Clos Vougeot and Lord Castlereagh, two of the darkest roses known; Chateau de Clos Vougeot was used as the female or seed parent and Lord Castlereagh as the male or pollen parent.

This new rose is much darker than either of its parents and is of a new shade, which to the best of my knowledge and belief has not before existed in roses, a deep violet which in some lights, or from a short distance, appears black. Compared with Ridgway color chart, the majority of petals check closely with Victoria Lake (and blacker) shown on Plate 1 and with blackish red purple (and darker) on Plate 12.

The following is a detailed description of this rose plant and flower, which have been asexually reproduced and in which the characteristics thereof are found to be permanently fixed:—

Parentage:—
Seedling.
*Seed parent.*—Chateau de Clos Vougeot.
*Pollen parent.*—Lord Castlereagh.
Classification:—
Hybrid Tea.

*Flower*

Blooming habit:—
*Recurrent.*—Continuous.
Bud:—
*Size.*—Medium.
*Form.*—Pointed.
*Color.*—Purple garnet, shaded black.
*Sepals.*—Pale green; stand out straight.
*Calyx.*—Shape—long, narrow; size—small; aspect—smooth on upper part, a few fine hairs around base.
*Peduncle.*—Medium length, covered with fine, widely spaced hairs.
*Opening.*—Opens well; does not ball.
Bloom:—
*Size.*—Medium 2½ to 3 inches.
*Borne.*—Singly.
*Stems.*—Medium; limber.
*Form.*—High pointed centre at first; almost flat when fully open, with outer petals folding their edges and curling backwards.
*Petalage.*—35 to 40.
*Color.*—Deep violet superimposed on dark crimson; varies from claret to blackish red purple depending upon conditions and seasons. The velvety pile on the petals is so deep that in certain lights the flower appears black. The backs of the petals retain the purple garnet with black shadings of the bud.
*Discoloration.*—The color becomes darker each day until the petals fall.
*Texture.*—Heavy.
*Appearance.*—Inside, velvety; outside, metallic.
*Form.*—Pear-shaped.
*Arrangement.*—Uniformly placed.
*Persistence.*—Drop off cleanly.
*Fragrance.*—Strong old Damask perfume.
*Lastingness.*—Average.
Genital organs:—
*Stamens, anthers.*—Few. Stamens, pink; anthers, yellow.
Color:—
*Pollen.*—Yellow.
*Styles.*—Bunched, uneven length, long, slender.
*Stigmas.*—Flesh colored.
*Ovaries.*—Normal.
Fruit:—
*Size.*—Small.
*Form.*—Round.
*Color.*—Light red hips.
*Seed.*—Contains 10 to 15.

*Plant*

Form:—Bush.
Growth:—Moderate, branching.
Foliage:—
*Size.*—Medium.
*Quantity.*—Normal.
*Color.*—New foliage: Upper side, maroon, under side, vinous purple. Mature foliage: Upper side, medium dark green; under side, pale green.
*Shape.*—Oval pointed.
*Texture.*—Leathery. Upper side, smooth; under side, rough. Ribs and veins ordinary.
*Edge.*—Serrated.
*Leaf stem.*—Color, green. Prickles on under side.
*Stipules.*—Medium size with pointed tips.
Wood:—
*New wood.*—Light green, smooth.
*Old wood.*—Light green, smooth.
Thorns:—
*Quantity.*—On main stalks quite numerous. On laterals ordinary.
*Form.*—Small base, slender, almost straight.
*Color when young.*—Pink.
*Position.*—Irregular.

I claim:—

The new variety of rose plant as disclosed, characterized by the distinct nearly black color of its bloom substantially as shown, and the persistence of this color, without fading, until the petals fall.

MAX KRAUSE.